United States Patent
Rauchschwalbe et al.

(10) Patent No.: US 9,512,298 B2
(45) Date of Patent: Dec. 6, 2016

(54) SPECIFIC MIXTURES OF N,N-BIS(2-HYDROXYALKYL)-4-TOLUIDINE DERIVATIVES, THEIR PREPARATION AND A METHOD OF USING SUCH SPECIFIC MIXTURES

(71) Applicants: Gunter Rauchschwalbe, Leverkusen (DE); Wolfgang Scheinert, Leverkusen (DE)

(72) Inventors: Gunter Rauchschwalbe, Leverkusen (DE); Wolfgang Scheinert, Leverkusen (DE)

(73) Assignee: LANXESS Deutschland GmbH, Cologne (DE)

( * ) Notice: Subject to any disclaimer, the term of this patent is extended or adjusted under 35 U.S.C. 154(b) by 0 days.

(21) Appl. No.: 13/723,493

(22) Filed: Dec. 21, 2012

(65) Prior Publication Data
US 2013/0116395 A1 May 9, 2013

Related U.S. Application Data

(63) Continuation of application No. 11/208,226, filed on Aug. 19, 2005, now abandoned.

(30) Foreign Application Priority Data

Sep. 4, 2004 (DE) .................. 10 2004 042 858

(51) Int. Cl.
*C08K 5/18* (2006.01)
*C07C 217/50* (2006.01)
*C08F 2/38* (2006.01)

(52) U.S. Cl.
CPC ............... *C08K 5/18* (2013.01); *C07C 217/50* (2013.01); *C08F 2/38* (2013.01)

(58) Field of Classification Search
USPC ........................................................ 525/447
See application file for complete search history.

(56) References Cited

U.S. PATENT DOCUMENTS 3,541,068 A * 11/1970 Taylor ........................... 523/116
2003/0083443 A1 * 5/2003 Santobianco et al. ........ 525/530

FOREIGN PATENT DOCUMENTS

RU      2063960 C1 * 7/1996

OTHER PUBLICATIONS

Wisniewski, M, Chemia Stosowana 32, 3-4, 503-514 1988.*
Sigma Aldrich product summary of p-Toluidine, no date.*
Freifelder et al, J. Org. Chem. 26 (1961), p. 1477-1480.*
Patent Board Decision in parent U.S. Appl. No. 11/208,226 dated Oct. 24, 2012.*

* cited by examiner

*Primary Examiner* — Alicia Bland

(57) ABSTRACT

A process is provided for preparing new mixtures of N,N-bis(2-hydroxyalkyl)-4-toluidine derivatives which can be used as polymerization accelerators.

7 Claims, No Drawings

SPECIFIC MIXTURES OF N,N-BIS(2-HYDROXYALKYL)-4-TOLUIDINE DERIVATIVES, THEIR PREPARATION AND A METHOD OF USING SUCH SPECIFIC MIXTURES

This application is a continuation of U.S. patent application Ser. No. 11/208,226 filed Aug. 19, 2005, incorporated herein by reference.

FIELD OF THE INVENTION

The invention relates to new mixtures of N,N-bis(2-hydroxyalkyl)-4-toluidine derivatives, to their preparation and to a method of using such mixtures comprising to their use as polymerization accelerators.

BACKGROUND OF THE INVENTION

The individual compound N,N-bis(2-hydroxyethyl)-4-toluidine is known. In J. Org. Chem. 26 (1961) 1477-1480 it is disclosed that it can be prepared by reacting 4-toluidine with 2 mol of ethylene oxide and then purified for example by distillation or crystallization. N,N-Bis(2-hydroxyethyl)-4-toluidine is obtained there in a yield of 76% of theory.

In Inorg. Chemie Acta 1995, 240, 257-62 as well the preparation of N,N-bis(2-hydroxyethyl)-4-substituted benzenes is described. N,N-Bis(2-hydroxyethyl)-4-toluidine is prepared by reacting 4-toluidine with 2-chloroethanol. Also described is the preparation of the individual compound N-(4-methylphenyl)azatetraglycol

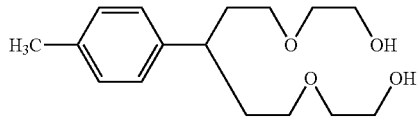 [SMILES: Cc1ccc(C(CCOCCO)CCOCCO)cc1]

by reaction of 4-toluidine with 2-(2-chloroethoxy)ethanol.

EP-A-1 256 615 discloses two-component adhesive compositions comprising an adhesive component and an activator component. Included in the adhesive component alongside the acrylic-/methacrylic-based monomers are reducing agents, which are optionally substituted anilines or optionally substituted toluidines. Substituted toluidines described are generally those of the formula

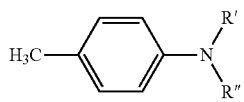

in which R' and R" can be identical or different and by reference to previous definitions can denote among other things $CH_2CHY_2$, in which Y, among numerous other definitions, can also be $OC_nH_{2n+1}$ with n less than 4. The sole explicit example of a correspondingly substituted para-toluidine is the individual substance N,N-bis(2-hydroxyethyl)-p-toluidine mentioned in Example 4 ("Emery 5710" from Cognis Corporation).

From WO-A-00/43425 it is known that N,N-bis(2-hydroxyethyl)-4-toluidine can be used as an accelerator for polymerizations or vulcanizations. Described therein is a redox initiator system for producing polyester granules by suspension polymerization, this redox initiator system comprising a diacyl peroxide and an aromatic amine of the formula

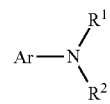

in which Ar is an optionally substituted aryl group and $R^1$ and $R^2$ are given a general definition and among other things can each be —(CHR'CHR'—O)$_n$H with n=1-10 and R' being H or $C_{1-3}$ alkyl. The preparation of commercially unavailable aromatic amines with polyoxyalkylene substituents on the nitrogen by reaction of the hydroxyalkyl compound with an alkylene oxide is said to be familiar to the skilled person. The sole explicitly cited substituted para-toluidine, which is also referred to as preferred, is, again, the individual substance N,N-bis(2-hydroxyethyl)-p-toluidine.

EP-A-1 070 730 describes how accelerators can be added for the rapid curing of methacrylate-based polymers. Condensation products of para-toluidine and ethylene oxide are specified for this purpose. Described explicitly is the product "Bisomer PTE" (International Specialty Chemicals), for which it is reported that two ethylene oxide units are located on each of the free valencies of the nitrogen.

US 2003/0083443 A1 discloses stabilized unsaturated polymer resin systems comprising a tertiary aromatic amine as vulcanization accelerator. The broad definition of the tertiary aromatic amine also embraces, on combination of the definitions of a very wide variety of substituents, tertiary aromatic amines having polyoxyalkylene substituents with 1-6 repeating oxyalkylene units on the nitrogen. Vulcanization accelerators specified as being preferred, however, are those which possess 3 different substituents on the nitrogen, of which only one is potentially a polyoxyalkylene substituent (paragraphs [0019] and [0026]). Here again, the sole substituted para-toluidine explicitly mentioned in the description is the individual substance N,N-bis(2-hydroxyethyl)-p-toluidine (paragraph [0075]). Furthermore, in Example 4, the product "Bisomer PTE" from International Speciality Chemicals is mentioned.

Chemia Stosowana 32, 3-4, 503-514 (1988) discloses the preparation of polyethoxylates of 4-alkylphenylamines by reaction of 4-alkylphenylamines with ethylene oxide in the presence of potassium hydroxide, a preparation which is investigated using as examples 4-hexyl-, 4-octyl-, 4-decyl-, 4-dodecyl- and 4-hexadecylphenylamine.

The object of the present invention was to provide a process by which further new N,N-bis(2-hydroxyalkyl)-4-toluidine derivatives can be obtained that can likewise be employed as polymerization accelerators or vulcanization accelerators.

SUMMARY OF THE INVENTION

This invention provides a process for preparing a mixture of two or more different compounds of the general formula (I)

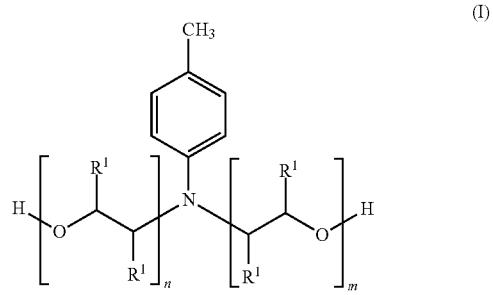

in which n and m independently of one another are each an integer in the range from 0 to 11, but the sum of n and m is at least 1, and $R^1$ radicals are identical or different and can be hydrogen or methyl, although two radicals $R^1$ located on directly adjacent carbon atoms are not simultaneously methyl, by reacting 4-toluidine, containing less than 0.2% by weight of 3-toluidine, based on 4-toluidine, with at least 2 mol of an alkylene oxide of the formula (II) per mole of 4-toluidine

(II)

where $R^1$ possesses the definition specified for the formula (I).

The invention also provides a mixture of two or more different compounds of the general formula (I) obtainable by this process.

DETAILED DESCRIPTION OF THE INVENTION

The process of the invention succeeds, surprisingly, in obtaining the mixtures of compounds of the general formula (I) with virtually complete conversion. At a gas chromatography detection limit of 100 ppm it is no longer possible to detect any unreacted 4-toluidine in the mixtures. This is of key importance, since the toluidines are strong blood poisons and are classified as being carcinogenic. The mixtures obtained are of excellent suitability as polymerization or vulcanization accelerators, preferably in the free-radical addition polymerization of polyesters and particularly of unsaturated polyesters. They lead, surprisingly, to no green or greenish discolouration of the polymer whatsoever, as is the case when similar mixtures are used that have been prepared, however, using 4-toluidine containing a 3-toluidine fraction of 0.2% by weight or more. Normally the available 4-toluidine possesses a 3-toluidine content of at least 0.2% by weight, since the preparation of 4-toluidine starts during the nitration of toluene, including the formation of the non-specification isomers 2- and 3-nitrotoluene, which distillation removes only to a certain extent, after which the remaining 4-nitrotoluene, which is even more highly contaminated, is subjected to hydrogenation.

In one preferred embodiment the process of the invention is carried out such that a 4-toluidine is used which contains 0.05% to 0.19%, more preferably 0.08% to 0.18%, in particular 0.08% to 0.15% and with particular preference 0.08%-0.12% by weight of 3-toluidine, based on 4-toluidine.

The inventive reaction of 4-toluidine having the stated maximum 3-toluidine content with at least and preferably more than 2 mol of ethylene oxide or propylene oxide per mole of 4-toluidine produces a mixture of different alkoxylated derivatives of N,N-bis(2-hydroxyethyl)-4-toluidine of the general formula (I) having different values of n and m. The mixture may contain not only compounds of the general formula (I) in which n and m are identical in the molecule, such as N,N-bis(2-hydroxyethyl)-4-toluidine or N,N-bis(2-hydroxyethyloxyethylene)-4-toluidine, but also compounds of the general formula (I) in which n and m possess different values in the molecule. The formulation "mixture of two or more different compounds of the general formula (I)" rules out the exclusive presence of a single substance such as N,N-bis(2-hydroxyethyl)-4-toluidine or N,N-bis(2-hydroxyethyloxyethylene)-4-toluidine.

The breadth of distribution of the mixture of the invention may be situated within narrow limits or may also have a relatively broad scatter in terms of the degree of alkoxylation n+m of the compounds present. This means, for clarification, that when x mol of alkylene oxide is used per mole of 4-toluidine, the mixture with the invention is found to contain not only compounds which have taken up x mol of alkylene oxide but also compounds of the general formula (I) which have taken up, for example, x−2, x−1, x, x+1 or x+2 mol of alkylene oxide. The corresponding distribution of the degree of alkoxylation can be determined by means of GC-MS. Using, for example, 3 mol of alkylene oxide per mol of 4-toluidine, i.e. starting from an average degree of alkoxylation of 3 molecules of alkylene oxide per molecule of 4-toluidine, the mixture of the invention may also include compounds of the general formula (I) which in total have taken up 1, 2, 3, 4, 5 and even 6 mol of alkylene oxide per molecule of 4-toluidine, i.e. compounds in which the sum of n and m amounts to 1, 2, 3, 4, 5 or 6.

The physical properties of the mixture of the invention of compounds of the general formula (I) can be adjusted within certain limits and adapted to the desired purpose by way of the degree of alkoxylation and of the resultant product distribution. N,N-Bis(2-hydroxyethyl)-4-toluidine is a solid (m.p. 53-54° C.), while the more highly alkoxylated derivatives of 4-toluidine are liquid at room temperature. Depending on the breadth of the distribution curve of the differently alkoxylated derivatives, therefore, it is possible in each case to prepare a mixture which is desired for the respective technical utility.

Mixtures of this kind of compounds of the general formula (I) which originate from a specific 4-toluidine have nowhere been described hitherto in the literature.

Ethylene oxide and propylene oxide can be used in commercially available form.

The process of the invention is carried out such that at least 2 mol, preferably more than 2 mol, more preferably 2.2 to 5 mol, very preferably 2.3 to 4 mol, in particular 2.3 to 3.5 mol and with particular preference 2.5-2.6 mol of ethylene oxide or propylene oxide are used per mole of 4-toluidine.

The process of the invention is carried out such that the alkylene oxide is introduced at an elevated temperature into a melt of 4-toluidine. Normally the reaction takes place at a temperature in the range from 100 to 170° C., preferably in the range from 110 to 160° C., more preferably in the range from 120 to 150° C. In one particular embodiment the reaction takes place in a closed apparatus under a slight superatmospheric pressure, thereby making it possible very largely to prevent the alkylene oxide escaping to the environment.

The process of the invention can be carried out in the presence of a catalyst, although it is equally possible to operate without catalyst. Catalysts which can be used during the alkoxylation are basic catalysts which are familiar in principle to the skilled person, preferably NaOH, KOH or NaOCH₃. The use of catalyst likewise makes it possible to control the product distribution in accordance with desire and technical purpose. The catalyst can be used in amounts of up to 1 mol %, preferably in the range of 0.05-1.0 mol %, based on the 4-toluidine used.

The use of ethylene oxide or propylene oxide as alkoxylating agent offers the advantage over other reagents (such as 2-chloroethanol) that there is no need to use auxiliary reagents (such as stoichiometric amounts of bases as HCl scavengers) and, accordingly, that there is no formation of salts that would have to have been separated off in a separate step.

In order to obtain the specific, particularly pure 4-toluidine of limited 3-toluidine content it is necessary to remove the 3-toluidine from the technical 4-toluidine by careful distillation, since the boiling points of the two isomers are close to one another (b.p. of 4-toluidine: 200.5° C.; b.p. of 3-toluidine: 203.4°).

A further possibility for preparing 4-toluidine having a 3-toluidine content of not more than 0.2% by weight is to recrystallize technical N-acetyl-4-toluidine, then to subject it to hydrolysis and to distillation.

4-Toluidine with a 3-toluidine content of less than 0.2% by weight is more preferably prepared by first nitrating toluene, effecting very thorough distillative separation of the two unwanted isomers, 2- and 3-nitrotoluene, from the resulting isomer mixture of 2-, 3- and 4-nitrotoluene, by optimizing the reflux ratio until the desired purity is obtained, and then subjecting the resultant 4-nitrotoluene to hydrogenation with the formation of 4-toluidine of the desired purity. In this way it is possible to make available even technical quantities of 4-toluidine having a 3-toluidine content of less than 0.2% by weight, preferably of less than 0.1% by weight.

The yield of the alkoxylation of the invention is virtually quantitative and is limited only by handling losses such as occur, for example, in the course of transfer as a result of adhesion of residual amounts to the reactor wall.

After the end of alkoxylation it has proven to be appropriate to cool the reaction mixture to a temperature in the range of 60-100° C. and to pass nitrogen over the reaction mixture for a certain period of time in order to remove any alkylene oxide that is present from the system completely.

The reaction mixture can be worked up by methods known to the skilled person or else can be used further directly.

The invention further provides for a method of using the mixture of the invention of two or more different compounds of the general formula (I) comprising preparing a polymer, preferably a polyester and more preferably an unsaturated polyester by a free-radical addition polymerization in the presence of the mixture of the invention as a polymerization accelerator or vulcanization accelerator. In this context it has proven to be appropriate to use the mixture of the invention in an amount of 0.1%-5% by weight.

The use of mixtures of this kind rather than single substances is advantageous since in the course of the preparation there are no losses of material as a result of purification, for example, at all.

As already mentioned, the mixtures prepared in accordance with the invention are notable for the fact that they can be used as polymerization or vulcanization accelerators in the production of colourless polymers, since their use leads to no discolouration of the polymer at all. This is of great importance depending on the desired application of the polymer, and is not achievable with arbitrary polymerization and vulcanization accelerators of the prior art.

EXAMPLES

Example 1

A 1-liter glass autoclave with stirrer, internal thermometer, inlet for ethylene oxide gas (dip tube with frit) and ascending tube for removal was initially charged with 321 g (3.0 mol) of 4-toluidine containing 0.1% by weight of 3-toluidine. The autoclave was rendered inert by being evacuated three times and injected again each time with 0.5 bar of nitrogen. Heating was carried out, initially without stirring, to 100° C., in order to melt 4-toluidine (m.p. 43° C.).

With a slight internal nitrogen overpressure, the batch was heated to the process temperature of 120° C. and 330 g (2.5 mol/mol of 4-toluidine) of ethylene oxide was introduced over the course of 10 hours with stirring. At 3-hour intervals the ascending tube was briefly flushed with nitrogen in order to mix back in fractions which had not undergone substantial reaction.

Stirring was continued for about 5 hours, the mixture was cooled to 80° C., the autoclave was let down and reduced pressure was applied. While stirring for three hours, residues of ethylene oxide were removed.

Thereafter the autoclave was flushed with nitrogen again and its contents were transferred to a receiver.

GC analysis showed that the product no longer contains 4-toluidine (detection limit: 100 ppm) and constituted a mixture of <0.1 area % of N-hydroxyethyl-4-toluidine, 50.1 area % of N,N-bis(hydroxyethyl)-4-toluidine and 43.7 area % of N-oxyethyl-N-(hydroxyethyloxyethylene)-4-toluidine, 5.4 area % of isomeric tetra- and 0.7 area % of isomeric pentaoxethylated and a trace of hexa-oxethylated isomers.

Example 2

An autoclave with stirrer, internal thermometer, immersive introduction tube for the ethylene oxide and ascending tube for removal was charged with 321 g (3.0 mol) of 4-toluidine containing 0.1% by weight of 3-toluidine, 1.0 g of 30% strength sodium methoxide solution was added and the autoclave rendered inert with nitrogen.

It was heated to 100° C. in order to melt the 4-toluidine, the stirrer was started and then 340 g of ethylene oxide (2.58 mol per mole of 4-toluidine) was introduced with stirring at 120° C. under an internal pressure of 1400 mbar, rising to 2510 mbar, over the course of 10 hours; at 3-hour intervals the ascending tube was blown clear in order to achieve uniform reaction.

Stirring was continued for 5 hours in order to achieve complete reaction, the autoclave was cooled to 80° C. and its contents were transferred to a receiver. This gave 630 g of product as a slightly viscous, yellowish, clear liquid. GC analysis showed that the product no longer contains any 4-toluidine (detection limit: 100 ppm) and no N-hydroxyethyl-4-toluidine; it contained a mixture of 47.4 area % of N,N-bis(hydroxyethyl)-4-toluidine, 43.4 area % of N-oxyethyl-N-(hydroxyethyloxyethyl)-4-toluidine and traces of more highly oxethylated compounds.

Example 3

The procedure of Example 2 was repeated but 400 g (3.0 mol/mol of 4-toluidine) of ethylene oxide were introduced; 690 g of product were obtained.

Example 4

The procedure of Example 2 was repeated but the reaction was carried out at 140° C. This gave 630 g of product.

Example 5

The procedure of Example 3 was repeated but adding KOH instead of NaOH. This gave 630 g of product.

Comparative Example 6

The procedure of Example 2 was repeated but using technical toluidine having a 3-toluidine content of 0.2% by weight. This gave 630 g of product.

Example 7

The procedure of Example 3 was repeated but using 4-toluidine obtained by acetylating technical 4-toluidine having a 3-toluidine content of 0.2% by weight, recrystallizing the product from a mixture of 2-propanol and water, subsequently hydrolysing the N-acetyl-4-toluidine and distilling the product.

Comparative Example 8

The procedure of Example 2 was repeated but ethoxylation was carried out using, as well as the 321 g (3.0 mol) of technically pure 4-toluidine having a 3-toluidine content of 0.1% by weight, additionally 1% by weight of 3-toluidine, based on the 4-toluidine.

Application Test:

The mixtures prepared in Examples 1-5 and 7 and also in Comparative Examples 6 and 8 were used in the application test below as polymerization accelerators. For this purpose an unsaturated polyester, Roskydal® K 14 M (brand name of Bayer AG), was admixed with 0.5% by weight of the respective mixture and polymerized with 3% by weight of benzoyl peroxide, based on the polyester.

The colouration of the polymer obtained was assessed on a scale of 0 to 5, where:
0: no green discolouration
1: weak greenish discolouration
2: slightly greenish
3: greenish
4: strong greenish discolouration

TABLE 1

| Mixture from example | Colouring of the polyester after polymerization in the presence of a mixture Score |
| --- | --- |
| 1 | 0 |
| 2 | 0 |
| 3 | 0 |
| 4 | 0 |
| 5 | 0 |
| Comparative Example 6 | 4 |
| 7 | 0 |
| Comparative Example 8 | 5 |

What is claimed is:

1. A method for preparing colorless polymer, the method comprising producing colorless polymer by free-radical addition polymerization of polymer precursors in a reaction mixture with a polymerization accelerator or vulcanization accelerator consisting of a mixture of two or more different compounds of general formula I:

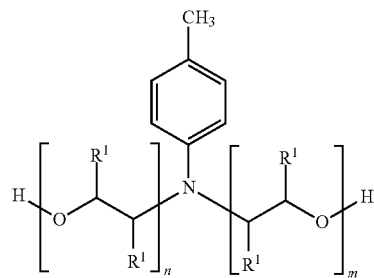

wherein:
n and m are each independently an integer from 0 to 11, wherein the sum of n and m is at least 1; and
each R1 is independently hydrogen or methyl, wherein two R1 located on directly adjacent carbon atoms are not both methyl; and
wherein each of the two or more compounds of the general formula I is prepared by reacting 4-toluidine, containing less than 02% weight of 3-toluidine based on the weight of the 4-toluidine, with an alkylene oxide of the formula (II)

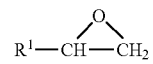

wherein each is independently hydrogen or methyl.

2. The method of claim 1, wherein n and m are identical in each respective compound.

3. A polymer prepared by the method of claim 1.

4. The method of claim 1, wherein the polymerization accelerator or vulcanization accelerator comprises 0.1%-5% by weight of the reaction mixture.

5. The method of claim 1, wherein the polymerization accelerator or vulcanization accelerator comprises N,N-bis(2-hydroxyethyl)-4-toluidine, N,N-bis(2-hydroxyethyloxyethylene)-4-toluidine, or combinations thereof.

6. The method of claim 1, wherein for at least one of the two compounds, n and m are different.

7. The method of claim 1, wherein the 4-toluidine contains 0.1% weight or less of 3-toluidine based on the weight of the 4-toluidine.

* * * * *